US006383740B2

(12) United States Patent
Collins

(10) Patent No.: US 6,383,740 B2
(45) Date of Patent: May 7, 2002

(54) METHODS FOR SIMULTANEOUSLY DETECTING BOTH MEMBERS OF A BINDING PAIR

(75) Inventor: Daniel P. Collins, Lino Lakes, MN (US)

(73) Assignee: BioErgonomics, Inc., St. Paul, MN (US)

(*) Notice: Subject to any disclaimer, the term of this patent is extended or adjusted under 35 U.S.C. 154(b) by 0 days.

(21) Appl. No.: 09/365,065

(22) Filed: Jul. 30, 1999

(51) Int. Cl.[7] .................................................. C12Q 1/70
(52) U.S. Cl. ......................... 435/5; 435/960; 435/968; 435/973; 435/974; 435/975; 436/501; 436/507; 436/518
(58) Field of Search ................................. 435/5, 6, 975, 435/973, 974, 968, 960; 436/518, 507, 501

(56) References Cited

U.S. PATENT DOCUMENTS

| 4,870,003 A | * 9/1989 | Kortright et al. ............... 435/5 |
| 5,091,206 A | 2/1992 | Wang et al. |
| 5,627,026 A | 5/1997 | O'Connor et al. |
| 5,776,709 A | * 7/1998 | Chandler et al. .......... 435/7.24 |
| 5,981,180 A | * 11/1999 | Chandler et al. ............... 435/6 |

FOREIGN PATENT DOCUMENTS

| EP | 0 351 248 | 1/1990 |
| WO | WO 99/19515 | 4/1999 |
| WO | WO 99/36564 | 7/1999 |

OTHER PUBLICATIONS

Collins, "Multi–system Approach to Analysis of T–Lymphocyte Activation by Flow Cytometry: Utilization of Intracellular Cytokine Expression, Cytokine Receptor Expression, and Quantification of Cytokine Secretion as an Indicator of Activation", *Clin. Immunol. Newsletter*, 1998, 18(11/12):140–145.

Multiplexed Cytokine Assays Sample Preparation Reagents Flow Cytometry Cellular Controls, BioErgonomics, Inc., St. Paul, MN, 1999, pp. 1–22.

Chan et al., "Quantum Dot Bioconjugates for Ultrasensitive Nonisotopic Detection", *Science*, 1998, 281:2016–2018.

Bruchez et al., "Semiconductor Nanocrystals as Fluorescent Biological Labels", *Science*, 1998, 281:2013–2015.

Spain, "Multiplexed testing for disease–marking synergies", *IVD Technology*, 1998, pp. 34–38.

Collins et al., "T–Lymphocyte Functionality Assessed by Analysis of Cytokine Receptor Expression, Intracellular Cytokine Expression, and Femtomolar Detection of Cytokine Secretion by Quantitative Flow Cytometry", *Cytometry*, 1998, 33:249–255.

Collins, "Multiplexed Cytokine Immunoassay for Flow Cytometry: A Powerful Tool for Studying T–Lymphocyte Function", *Biomedical Products Online*, Jun. 1999, pp. 1–4.

Package insert of Coulter HIV–1 p24 Antigen Assay. 1996.

Constantine, "HIV Viral Antigen Assays," HIV InSite Knowledge Base Chapter. 1998. http://hivinsite.ucsf.edu/InSite.jsp?page=kb–02–02–02–02.

Constantine, "HIV Antibody Assays," HIV InSite Knowledge Base Chapter. 1998. http://hivinsite.ucsf.edu/InSite.jsp?page=kb–02–02–01.

* cited by examiner

Primary Examiner—Donna Wortman
Assistant Examiner—Robert A. Zeman
(74) Attorney, Agent, or Firm—Fish & Richardson, P.C.

(57) ABSTRACT

Methods and kits for simultaneously measuring both members of a binding pair are described.

20 Claims, 3 Drawing Sheets

METHODS FOR SIMULTANEOUSLY DETECTING BOTH MEMBERS OF A BINDING PAIR

Technical Field

The invention relates to methods for simultaneously detecting both members of a binding pair in a biological sample.

Background of the Invention

Blood products used for transfusion and transfer of blood components must be routinely screened for the presence of infectious agents such as human immunodeficiency virus (HIV), hepatitis viruses, human T-lymphocytotropic virus, and cytomegalovirus. Such agents typically are detected by either identification of viral antigens or by detection of an immune response to the virus (i.e., host-derived antiviral antibodies) using enzyme immunoassay analysis (EIA) or radioimmunoassays (RIA). Immunoassay techniques are limited in their ability to detect the presence of viral contaminants in early stages of infection, with the window period between infection with a virus and detection by immunoassay techniques varying from two to four weeks for HIV and up to about 10 weeks for hepatitis C virus (HCV). Techniques such as reverse-transcriptase polymerase chain reaction (RT-PCR) or branched chain DNA analysis can shorten the time period between infection and detection, but are cost prohibitive for use on an individual donor basis and do not eliminate the window period.

Summary of the Invention

The invention is based on a rapid and sensitive method for simultaneously detecting both members of a binding pair, such as a ligand and receptor or an antigen and host antibody, from a biological sample. Methods of the invention can, for example, enhance the ability to detect infections at an early stage, leading to earlier treatment of the infection.

The invention features a method for simultaneously measuring both members A and B of a binding pair in a biological sample. The biological sample is selected from the group consisting of blood, plasma, serum, urine, cerebrospinal fluid, sputum, tears, amniotic fluid, vitreous humor, saliva, and tissue culture supernatants. The method includes providing a solid phase reagent, which includes a particle coated with capture antibodies having specific binding affinities for member A of the binding pair, and contacting a biological sample with the solid phase reagent under conditions in which member A, if present, becomes bound to the particle, to form a first reacted particle. The capture antibodies can be monoclonal. The first reacted particle is contacted with first antibodies having specific binding affinities for member A, wherein the first antibodies are labeled with a first label, and with second antibodies having specific binding affinities for member B of the binding pair, wherein the second antibodies are labeled with a second label, to form a second reacted particle. The first and second antibodies can be monoclonal. First and second labels (e.g., fluorophores) are measured on the second reacted particle using flow cytometry.

In certain embodiments, substantially all capture antibodies are oriented on the particle such that the antigen binding regions of the capture antibodies are available for binding member A of the binding pair.

Member A of the binding pair can be, for example, an antigen and member B can be a host antibody. The antigen can be a viral antigen such as a hepatitis C antigen, a hepatitis B antigen, or a human immunodeficiency virus antigen, or an autoantigen such as glutarnic acid decarboxylase. Member A of the binding pair also can be a ligand, such as a cytokine, and member B can be a receptor, such as a cytokine receptor. In addition, member A can be an enzyme and member B can be a substrate. For example, the enzyme can be caspase-3 or caspase-1 and the substrate can be poly(ADP-ribose) polymerase or proInterleukin-1, respectively.

The invention also features a kit for simultaneously measuring both embers A and B of a binding pair in a biological sample. The kit includes a solid phase reagent, which includes a particle coated with capture antibodies having specific binding affinities for member A of the binding pair; first antibodies having specific binding affinities for member A of the binding pair, wherein the first antibodies are labeled with a first label; and second antibodies having specific binding affinities for member B of the binding pair, wherein the second antibodies are labeled with a second label. Substantially all the capture antibodies are oriented on the particle such that the antigen binding regions of the capture antibodies are available for binding member A of the binding pair. The kit further can include a label or package insert, which indicates that the solid phase reagent, the labeled first antibodies, and the labeled second antibodies can be used for simultaneously measuring both members A and B of a binding pair in a biological sample by flow cytometry.

Unless otherwise defined, all technical and scientific terms used herein have the same meaning as commonly understood by one of ordinary skill in the art to which this invention belongs. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

Brief Description of the Drawings

FIG. 2A is HBV antigen and antibody in a normal sample.

FIG. 2B is HCV antigen and antibody in a normal sample.

FIG. 2C is HBV antigen and antibody in an HBV positive sample.

FIG. 2D is HCV antigen and antibody in an HBV positive sample.

FIG. 2E is HBV antigen and antibody in an HCV positive sample.

FIG. 2F is HCV antigen and antibody in an HCV positive sample.

FIG. 2G is HBV antigen and antibody in an HBV positive/HCV positive sample.

FIG. 2H is HCV antigen and antibody in an HBV positive/ HCV positive sample.

DETAILED DESCRIPTION

Immunoassay Format

Figure 1:
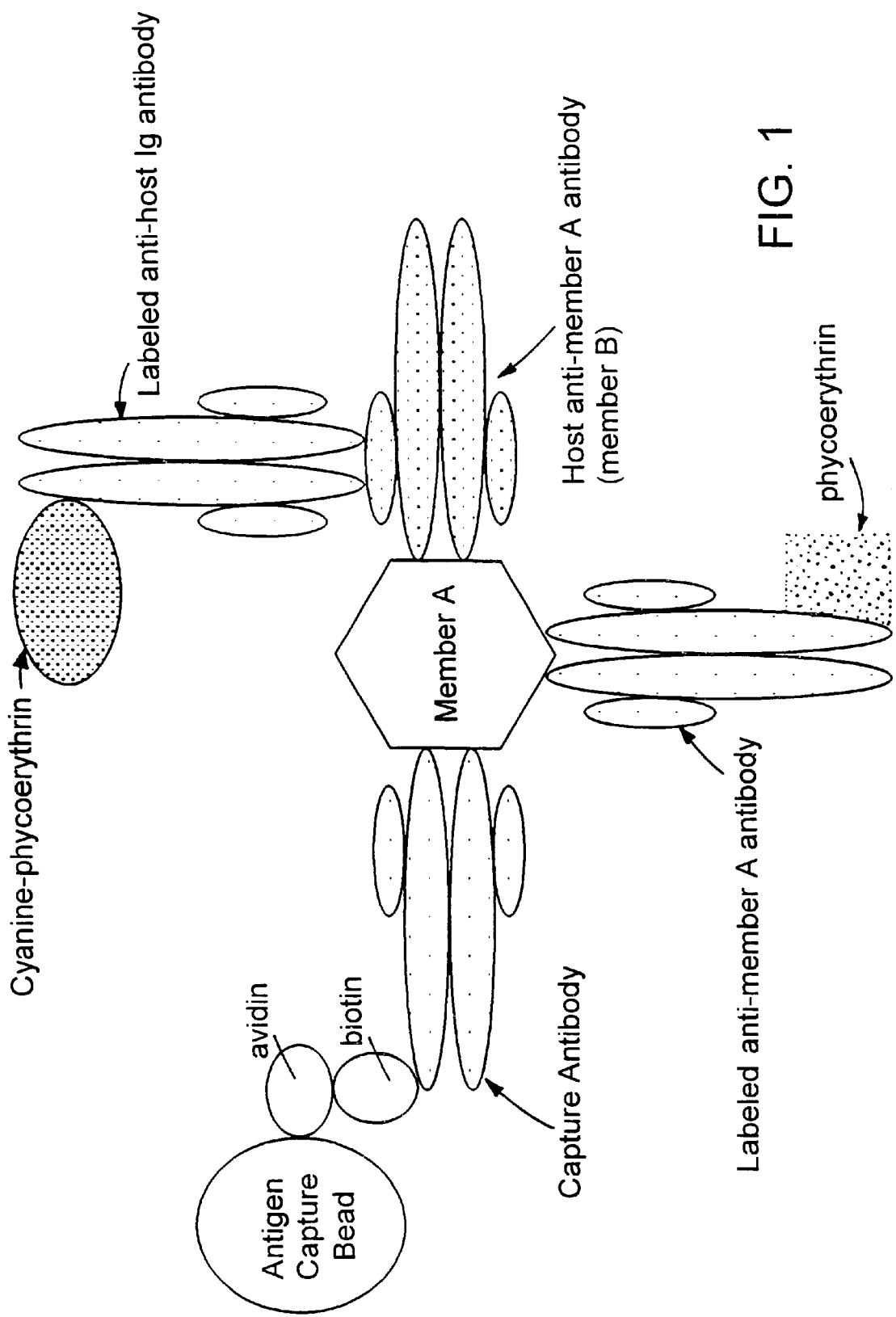
FIG. 1 is a schematic representation of an assay for detecting member A and host anti-member A antibody (member B).
Figure 2A:
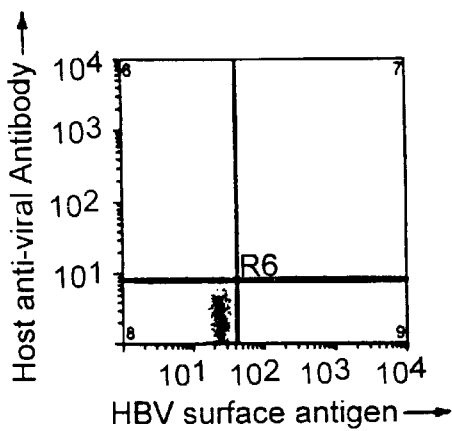
FIGS. 2A–2H are scattergrams that indicate simultaneous detection of hepatitis B virus (HBV) surface antigen, anti-HBV host antibody, HCV core antigen, and anti-HCV host antibody by flow cytometry.
Figure 2B:
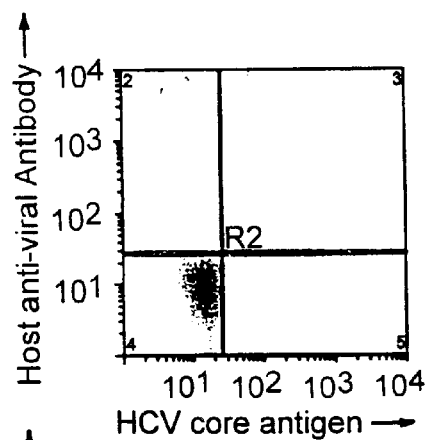
Figure 2C:
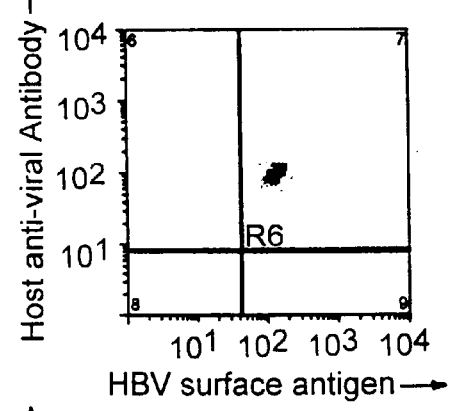
Figure 2D:
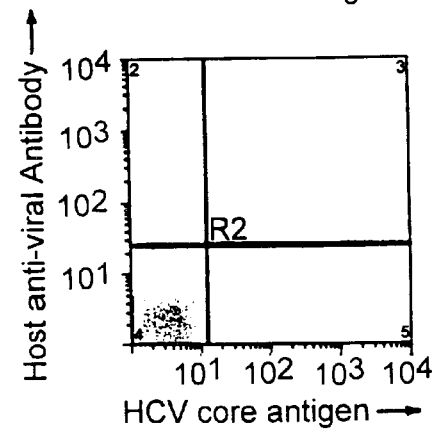
Figure 2E:
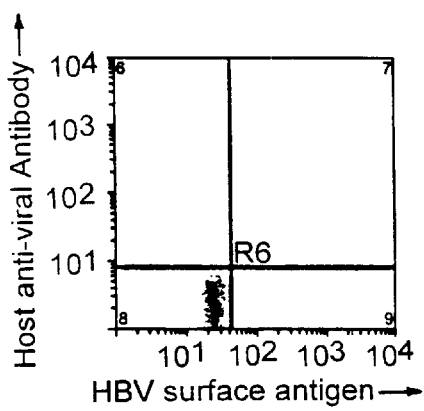
Figure 2F:
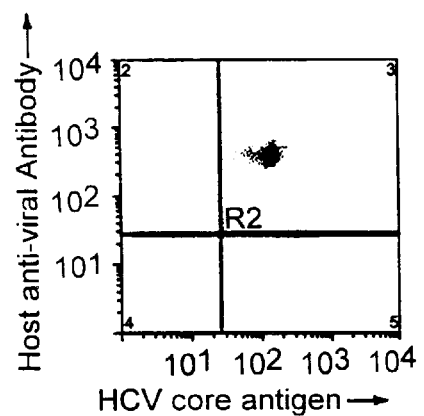
Figure 2G:
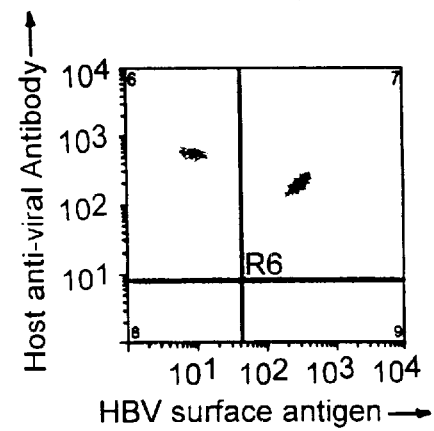
Figure 2H:
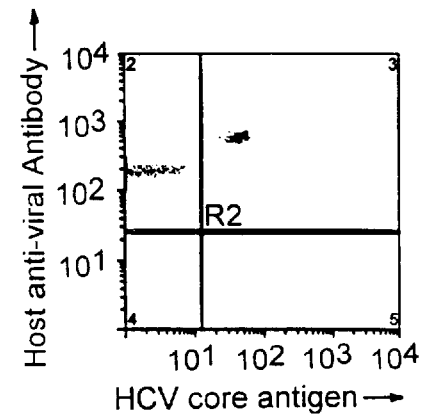

In general, the invention uses a sandwich immunoassay method for simultaneously detecting both members of a binding pair in a biological sample. Binding pairs include any combination of molecules which forms a complex, including pairs composed of nucleic acids, proteins, or a small molecule and a protein. Nucleic acid pairs can be DNA:RNA pairs or DNA:DNA pairs. For example, a DNA/RNA binding pair such as a single stranded (ss) DNA and an mRNA can be used as a PCR product detection system. A DNA/DNA binding pair such as a ssDNA and a viral DNA can be used in a competition assay for quantitation of virus per amplified DNA.

Non-limiting examples of protein, or small molecule and protein, binding pairs include a hormone, a cytokine, a peptide, a drug, a viral protein, or other antigen and a cognate receptor or host antibody. Viral protein/receptor binding pairs can be, for example, HIV gp120 and soluble CD4. Drug and drug receptor binding pairs can be, for example, cocaine and a dopamine receptor. Peptide and peptide receptor binding pairs can be, for example, acetylcholine and a muscarinic receptor or dopamine and a dopamine receptor. Hormone and hormone receptor binding pairs can be, for example, insulin and insulin receptor. Cytokine and cytokine receptor binding pairs can be, for example, tumor necrosis factor (TNF) and a TNF Type I or Type 2 receptor or interleukin 2 (IL-2) and IL-2 receptor. Antigen and antibody pairs can be, for example, a viral protein and host anti-viral protein antibody or an autoantigen and a host anti-autoantigen antibody. HIV p24/human anti-HIV antibody, HIV gp120/human anti-HIV gp120 antibody, HBV surface antigen/human anti-HBV surface antigen, and HCV core protein/human anti-HCV core antibody are examples of viral protein and host antibody binding pairs. An autoantigen and host anti-autoantigen antibody binding pair can be, for example, glutamic acid decarboxylase (GAD) and host anti-GAD antibody.

Other protein binding pairs that can be detected are enzyme and enzyme substrate binding pairs. For example, the enzyme/substrate pair can be caspase-3/poly (ADP-ribose) polymerase or caspase-1/proInterleukin-1.

Member A, which can be either member of the binding pair, is captured with a solid phase reagent that is a particle coated with capture antibodies having specific binding affinities for member A. For example, if the binding pair to be simultaneously detected is HIV gp120/host anti-HIV gp120 antibody, the particle can be coated with antibodies having specific binding affinities for HIV gp120 or anti-host immunoglobulin (Ig).

Member A is captured by contacting a biological sample with the particle coated with capture antibodies. As used herein, suitable biological samples contain cells or cellular material, and include, for example, blood, plasma, serum, urine, saliva, sputum, tears, amniotic fluid, vitreous humor, and cerebrospinal fluid. Other samples can include in vitro tissue culture medium/supernatants. Biological samples can be treated with a non-ionic detergent such as 0.5% Triton-X 100 or Nonidet P40 (Sigma Chemical Company, St. Louis, Mo.) to expose core antigens from pathogens.

The solid phase reagent and biological sample are contacted under conditions that facilitate binding of member A, if present, to the particle, to form a first reacted particle. Such conditions can include use of buffer containing 1% fetal bovine serum (FBS) and 0.1% sodium azide in phosphate-buffered saline (PBS) at room temperature, or use of any biological fluid, under physiologic pH conditions. The first reacted particle then is contacted with two sets of labeled antibodies (i.e., reporter antibodies) to form a second reacted particle. The first antibodies have specific binding affinities for member A and are labeled with a first label. First antibodies are capable of binding to member A while member A is bound to capture antibodies. Thus, the capture antibodies and first antibodies must work as a pair. Second antibodies have specific binding affinities for member B of the binding pair and are labeled with a second label. Fluorescently labeled antibodies are particularly useful in this method.

FIG. 1 provides a schematic of an assay for detecting member A and host anti-member A antibody. In this embodiment, biotinylated capture antibodies have specific binding affinities for member A and are coupled to antigen capture beads via avidin. First antibodies have specific binding affinities for member A and are labeled with phycoerythrin (first label). Second antibodies are labeled with cyanine-phycoerythrin (second label) and have specific binding affinities for host Ig (member B). The first reacted particle includes member A, host anti-member A antibodies, capture antibodies, and the solid phase reagent (e.g, antigen capture beads), wherein the second reacted particle includes the first reacted particle and the two labeled antibodies.

Flow cytometry can be used to measure the amount of label on the second reacted particle. As used herein, the term "measure" refers to qualitative and quantitative measurements. In other words, the term "measure" includes reporting the presence or absence of label on the second reacted particle, as well as determining the amount of label present. Flow cytometers are able to measure at least three discrete fluorescence emission wavelength ranges by using optical filters to split the fluorescent emission and separate photomultiplier tubes to amplify the individual emission signals. The intensity of fluorescent emission associated with the particles is directly proportional to the concentration of analyte present in the biological sample. Thus, the use of different dyes with different emission spectra, wherein each dye is coupled to a different antibody, allows analysis of multiple analytes per population of particles. The flow cytometer also can distinguish particles of different sizes such that a particle, for example approximately 7 μm in diameter, can be differentiated from a particle approximately 10 μm in diameter. Therefore, additional components can be detected by using a combination of multiple fluorescent dyes and two or three populations of particles of different average diameters.

Production of Antibodies

Antibodies having specific binding affinities for member A or member B can be produced through standard methods. Alternatively, antibodies may be commercially available, for example, from BiosPacific (Emeryville, Calif.), Coulter (Hialeah, Fla.), Maine Biotechnology Service (Portland, Me.), or Biodesign International (Kennebunk, Me.). As used herein, the terms "antibody" or "antibodies" include intact molecules as well as fragments thereof which are capable of binding to an epitopic determinant in member A or member B. The term "epitope" refers to an antigenic determinant on an antigen to which the paratope of an antibody binds. Epitopic determinants usually consist of chemically active surface groupings of molecules such as amino acids or sugar side chains, and typically have specific three dimensional structural characteristics, as well as specific charge characteristics. Epitopes generally have at least five contiguous amino acids. Thus, the terms "antibody" and "antibodies" include polyclonal antibodies, monoclonal antibodies, humanized or chimeric antibodies, single chain Fv antibody fragments, Fab fragments, and $F(ab)_2$ fragments. Monoclonal antibodies are particularly useful.

In general, a protein of interest is produced recombinantly, by chemical synthesis, or by purification of the native protein, and then used to immunize animals. Various host animals including, for example, rabbits, chickens, mice, guinea pigs, and rats, can be immunized by injection of the protein of interest. Adjuvants can be used to increase the immunological response depending on the host species and include Freund's adjuvant (complete and incomplete), mineral gels such as aluminum hydroxide, surface active substances such as lysolecithin, pluronic polyols, polyanions, peptides, oil emulsions, keyhole limpet hemocyanin (KLH), and dinitrophenol. Polyclonal antibodies are heterogenous populations of antibody molecules that are specific for a particular antigen, which are contained in the sera of the immunized animals. Monoclonal antibodies, which are homogeneous populations of antibodies to a particular epitope contained within an antigen, can be prepared using standard hybridoma technology. In particular, monoclonal antibodies can be obtained by any technique that provides for the production of antibody molecules by continuous cell lines in culture such as described by Kohler, G. et al., *Nature*, 1975, 256:495, the human B-cell hybridoma technique (Kosbor et al., *Immunology Today*, 1983, 4:72; Cole et al., *Proc. Natl. Acad. Sci. USA*, 1983, 80:2026), and the EBV-hybridoma technique (Cole et al., "Monoclonal Antibodies and Cancer Therapy", Alan R. Liss, Inc., 1983, pp. 77–96). Such antibodies can be of any immunoglobulin class including IgG, IgM, IgE, IgA, IgD, and any subclass thereof. The hybridoma producing the monoclonal antibodies of the invention can be cultivated in vitro or in vivo.

A chimeric antibody is a molecule in which different portions are derived from different animal species, such as those having a variable region derived from a murine monoclonal antibody and a human immunoglobulin constant region. Chimeric antibodies can be produced through standard techniques.

Antibody fragments that have specific binding affinity for member A or B can be generated by known techniques. For example, such fragments include, but are not limited to, $F(ab')_2$ fragments that can be produced by pepsin digestion of the antibody molecule, and Fab fragments that can be generated by reducing the disulfide bridges of $F(ab')_2$ fragments. Alternatively, Fab expression libraries can be constructed. See, for example, Huse et al., 1989, *Science*, 246:1275. Single chain Fv antibody fragments are formed by linking the heavy and light chain fragments of the Fv region via an amino acid bridge (e.g., 15 to 18 amino acids), resulting in a single chain polypeptide. Single chain Fv antibody fragments can be produced through standard techniques. See, for example, U.S. Pat. No. 4,946,778.

Once produced, antibodies or fragments thereof are tested for recognition of member A or member B by standard inmnunoassay methods including, for example, ELISA techniques or RIA. See, *Short Protocols in Molecular Biology*, Chapter 11, Green Publishing Associates and John Wiley & Sons, Edited by Ausubel, F.M et al., 1992. Suitable antibodies preferably have equal binding affinities for recombinant and native proteins.

Alternatively, antibodies can be assessed for their ability to form binding pairs in a fluorescent sandwich assay in the following manner. Beads can be coated with biotinylated antibodies, for example anti-viral protein antibodies, then incubated for approximately 30 minutes with 2 ng/ml of the appropriate protein, e.g., recombinant viral protein, in a 100 $\mu$l volume. After washing the beads twice with 2 ml of buffer containing 1% FBS and 0.1% sodium azide in PBS, the beads are incubated with approximately 0.5 $\mu$g of phycoerythrin-labeled antibody. Pairs of antibodies producing a strong fluorescent signal are suitable for use in assays of the invention.

Solid Phase Reagents

Suitable particles (e.g, beads) have an average diameter of about 2 $\mu$m to 15 $\mu$m and can be polystyrene, ferromagnetic, or paramagnetic. For example, the particles can have an average diameter of about 4 $\mu$m to about 11 $\mu$m. Typical average particle diameters are about 4–5 $\mu$m, 7–8 $\mu$m, and 10–11 $\mu$m. Particles are available commercially, for example, from Spherotech Inc., Libertyville, Ill. Particles can be coated with capture antibodies by known techniques. For example, avidin- or streptavidin-coated paramagnetic beads can be coated with biotinylated capture antibodies. In general, avidin- or streptavidin-coated beads are resuspended in a saline solution, such as PBS, mixed with biotinylated antibodies at saturating conditions (approximately 40 $\mu$g of protein per $3.9 \times 10^7$ 7 $\mu$m beads), and incubated at room temperature. After binding is complete, the beads are washed and blocked with, for example, buffer containing 1% FBS and 0.1% sodium azide in PBS.

Avidin- or streptavidin-coated beads can be coupled to biotinylated nucleic acids when nucleic acid binding pairs are being measured. Nucleic acids can be labeled with biotin by incorporation of biotin-11-dUTP in a standard nick translation reactions.

In particular embodiments, substantially all of the capture antibodies are oriented on the particle such that the antigen binding regions are available for binding member A, increasing overall sensitivity of the assay. The term "substantially all" indicates that at least 80%, and preferably at least 90%, (e.g., 95% or 99%) of the antibodies are oriented in this fashion. Percent orientation can be estimated qualitatively by measuring fluorescence associated with binding of phycoerythrin-labeled goat anti-mouse antibody, and comparing with standardized fluorescent particles. Antigen binding regions of antibodies are available for binding member A when the antibody is biotinylated at amino acid residues primarily outside of the antigen binding region. Thus, during biotinylation of antibodies, a molar ratio of biotin:antibody of about 5:1 to about 10:1 and other standard reaction conditions are used. For example, biotin N-hydroxysuccinimidyl ester or biotin succinimidyl ester can be used at a pH of about 8.1. Alternatively, biotin hydrazide can be used at a pH of 4.5–5.0.

Assay sensitivity also is increased because capture of member A from a biological sample is not limited to reaction volumes of 200 $\mu$l or less, as in traditional assays. Particles are easy to collect from large volumes of biological sample by either magnetic separation or centrifugation. Furthermore, each particle contains, on average, approximately 180,000 to 240,000 antibody binding sites, and approximately 300,000 to 350,000 biotinylated antigen binding sites per particle. Thus, each particle has a large binding capacity and a large effective range of analysis for antigen concentration.

Detectable Labels

Each labeled antibody can be distinctly visualized by labeling with a fluorophore that emits light of a color that contrasts with other fluorophores. For example, a combination of the following fluorophores may be used: 7-amino-4-methylcoumarin-3-acetic acid (AMCA), Texas Red™ (Molecular Probes, Inc., Eugene, OR), 5-(and-6)-carboxy-X-rhodamine, lissamine rhodamine B, 5-(and-6)-carboxyfluorescein, fluorescein-5-isothiocyanate (FITC), 7-diethylaminocoumarin-3carboxylic acid, tetramethylrhodamine-5-(and-6)-isothiocyanate, 5-(and-6)-carboxytetramethylrhodamine, 7-hydroxycoumarin-3-carboxylic acid, 6-[fluorescein 5(and-6)-carboxamido] hexanoic acid, N-(4,4-difluoro-5,7-dimethyl-4-bora-3a,4a diaza-3-indacenepropionic acid, eosin-5-isothiocyanate, erythrosin-5-isothiocyanate, phycoerythrin (B-, R-, or cyanine-), allophycocyanin, Oregon Green™, and Cascade™ blue acetylazide (Molecular Probes, Inc., Eugene, Oreg.).

Antibodies also can be labeled with semiconductor nanocrystals. Water soluble nanocrystals are composed of different sizes of cadmium-selenium/cadmiumsulfur core-shell nanocrystals enclosed in a silica shell or cadmium-selenium/zincsulfur nanocrystals solubilized in mercaptoacetic acid. Such water soluble nanocrystals have a narrow, tunable, symmetric emission spectrum and are photometrically stable. See, Bruchez Jr. et al., *Science*, 1998, 281:2013–2016; and Chan et al., *Science*, 1998, 281:2016–2018.

Detection of Multiple Antigens and Host Antibody

A combination of labels, such as Oregon Green™ (Molecular Probes, Inc., Eugene, Oreg.), phycoerythrin, and cyanine-phycoerythrin, can be used to detect, inter alia, two antigens and a host antibody. For example, HCV, HBV surface antigen, host anti-HCV antibody, and host anti-HBV surface antigen antibody can be simultaneously detected using phycoerythrin-labeled antibodies having specific binding affinities for HCV, Oregon Green™-labeled antibodies having specific binding affinities for HBV surface antigen, and cyanine-phycoerythrin-labeled anti-host Ig antibodies. Using three different labels and two populations of particles having different sizes (e.g., average diameters of 7–8 µm and 10–11 µm) allows up to 6 different viral antigens and host antibodies to be detected simultaneously. Use of a third population of particles of a different average diameter allows up to 9 different viral antigens and host antibodies to be detected.

Viral antigens can be difficult to detect in plasma samples once an individual has seroconverted (i.e, has developed host antibodies) because the binding sites for the capture or reporter antibodies on the viral particle have been blocked by the host antibody. The present invention overcomes this difficulty due to the improved sensitivity of the assay over traditional immunoassay formats. Thus, viral antigen can be detected using the present methods in situations in which traditional immunoassay formats cannot do so. As described herein, viral antigens can be captured using particles coated with monoclonal antibodies having specific binding affinities for the viral protein, and their presence detected with reporter monoclonal antibodies directed against the viral protein in seropositive individuals. Host antibody directed against the viral protein can be simultaneously detected through labeled goat anti-human Ig. Detection of viral protein without host antibody indicates the host was recently infected and has not seroconverted, while detection of viral protein and host antibody indicates the presence of infection as well as seroconversion. In certain samples, host antibody may be detected but viral protein is not when, for example, binding sites for the first antibody are not available. Although viral proteins are not directly measured in this instance, viral proteins are still present in the sample, as the antibody-coated capture bead directed against the viral protein captures the immune complex of viral antigen and host antibody.

The invention will be further described in the following examples, which do not limit the scope of the invention described in the claims.

EXAMPLES

Example 1

Biotinylation of Proteins

Antibodies were conjugated at a concentration of 5 mg/ml; viral antigens were conjugated at a concentration of 1 mg/ml. To biotin label anti-viral protein antibodies and viral antigens, the proteins were exchanged into 100 mM $KH_2CO_3$ buffer (pH 8.3) using an appropriate size Centricon (Amicon) filter.

Biotin N-hydroxysuccinimidyl ester (Molecular Probes, Eugene, Oreg.) in DMSO (10 mg/ml, Sigma Chemical Co., St. Louis, Mo., Cat. #D8779) was prepared immediately prior to use, and added to the protein to be biotinylated in a 5:1 or 10:1 molar ratio. Reactions were performed by vortexing the protein solution lightly, and adding the biotin/DMSO to the protein solution and mixing thoroughly. Protein and biotin ester were reacted for one hour at room temperature in the dark. Conjugated protein was separated from free biotin by separation on a 10 ml Sephadex-25 gel column or spin column using 1×PBS to elute. Individual 1 ml fractions were collected and absorbance at A280 nm was measured. Fractions representing the initial peak of A280 were collected and pooled, while remaining fractions, including those representing the second A280 peak, were discarded.

When spin columns were used, the reaction mixture was distributed equally between four spin columns, and spun using a Serofage centrifuge on high speed for 2 mins. Material passing through the column was collected and the columns were washed by filling the column with 1×PBS and spinning at high speed in a Serofuge for 2 min and repeating five times. Collected material was redistributed equally among four columns, then spun using the Serofage centrifuge on high speed for 2 min. Material passing through the column was collected, pooled, and re-analyzed for A280 and the concentration was determined. Conjugated protein was stored at 4° C.

Example 2

Production of Analyte Capture Beads

Analyte capture beads were prepared by completely resuspending avidin-coated paramagnetic beads (7 µm, Spherotech, VM-60-100) by mixing well. Beads (typically $3.8 \times 10^6$ beads) were placed in a 50 ml centrifuge tube and mixed with 30 ml of 1×PBS. After retaining beads on the side of the tube with magnets, all PBS was removed. The beads were washed two more times with PBS.

After the final PBS wash, the required volume of biotinylated antibody (typically 40 µg) and 2 ml of 1×PBS were added to the beads. The beads were resuspended by vortexing continuously for a minimum of 3 hours, or by vortexing for one hour and then storing overnight at 4° C. Beads stored overnight were vortexed for an additional 2 hours the next morning. Approximately 30 ml of buffer containing 1% FBS and 0.1% NaN₃ in PBS were used to wash the conjugated beads three times. Beads were resuspended in 19.25 ml of the same buffer and stored at 4° C. until use.

To label antibodies with the fluorescein derivative Oregon Green™ (Molecular Probes, Eugene, Oreg.), antibodies were exchanged into 100 mM $KH_2CO_3$ buffer (pH 9.0) at a concentration of 5 mg/ml. Oregon Green™ (10 mg/ml in dimethylformamide, DMF) was added to the antibody at a 25:1 molar ratio and incubated for 1 hour at room temperature, in the dark. Free Oregon Green™ was separated from the antibody on a G-25 Sephadex column. R-phycoerythrin (PE, Intergen BioDiagnostics, Purchase, N.Y.) and cyanine-phycoerythrin (CySPE) conjugates were produced using 2-iminothiolane (Pierce Chemical Co., Rockford, Ill.) in a 1625:1 molar ratio to modify the fluorochrome and sulfo-SMCC (Pierce) in a 20:1 molar ratio to modify the antibody. Modified fluorochrome and antibody were incubated together for 1 hour at room temperature in the dark. Free fluorochrome and antibody were separated from fluorochrome-conjugated antibody on Sephacryl S-300-HR columns (Sigma Chemical Co., St. Louis, Mo.). Goat F(ab')₂ anti-human Ig antiserum (heavy and light chain specific) affinity-purified and absorbed against mouse, equine, bovine, rat, and rabbit antibodies was labeled with PE or Cy5-PE. Alterations in the ratio of fluorochrome to protein can be made to optimize the fluorescent signal for a particular antibody or viral antigen.

Example 3

Detection of Viral Antigens and Host Antibody

Plasma samples from normal individuals and from individuals positive for HCV, HIV, or HBV were obtained from New York Biologicals (Southampton, N.Y.), Scantibodies Laboratory (Santee, Calif.), or Intergen BioDiagnostics (Purchase, N.Y.). Plasma samples were treated with Triton-X 100 detergent to a final concentration of 0.5% to lyse viral membranes and expose core particles prior to testing. *E. coli* derived recombinant viral antigens, including surface and core antigens, were obtained from BiosPacific (Emeryville, Calif.) or Intergen BioDiagnostics. Antigens were added to normal nonpathologic serum samples for development of a reference standard curve and for use in spike and recovery analysis.

Flow cytometric analysis was performed on a Coulter EPICS Profile II, a Coulter XL, or a Partec PAS flow cytometer using linear forward vs. side light scatter to gate the bead population. Fluorescence signal was amplified logarithmically. Fluorescence emissions were segregated into discrete colors by optical filters. A 525 nm bandpass filter was used to collect the green fluorescence (Oregon Green and FITC), a 565 nm bandpass filter to collect the orange fluorescence (PE), and a 630 nm long pass filter to collect the red fluorescence (Cy5 PE).

Samples were incubated with PE- and Cy5PE-labeled F(ab')₂ goat anti-human Ig (heavy and light chain specific) antibody. In each case, host anti-viral antibodies were detected on beads with captured antigen and not on beads from normal samples or an incorrect virus. BBV surface antigen and anti-HBV antibody, as well as HCV core antigen and anti-HCV antibody, were detected using a PE labeled antibody having specific binding affinity for HCV core antigen, an Oregon Green labeled antibody having specific binding affinity for HBV surface antigen, and a CySPE labeled goat anti-human Ig antibody. As indicated in FIGS. 2A–2H, individual and simultaneous detection of HCV, HBV, and host antibody were possible.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for simultaneously measuring both members A and B in a binding pair complex in a biological sample, said method comprising:

a) providing a solid phase reagent, said solid phase reagent comprising a particle coated with capture antibodies having specific binding affinities for said member A of said binding pair complex;

b) contacting said biological sample with said solid phase reagent under conditions in which said member A, if present, becomes bound to said particle, to form a first reacted particle:

c) contacting said first reacted particle with first antibodies having specific binding affinities for said member A, wherein said first antibodies are labeled with a first label, and with second antibodies having specific binding affinities for said member B of said binding pair complex, wherein said second antibodies are labeled with a second label, to form a second reacted particle, wherein said first and second labels are different and d) measuring said first and second labels on said second reacted particle using flow cytometry.

2. The method of claim 1, wherein substantially all said capture antibodies are oriented on said particle such that the antigen binding regions of said capture antibodies are available for binding said member A of said binding pair complex.

3. The method of claim 1, wherein said member A is an antigen and said member B is a host antibody.

4. The method of claim 3, wherein said antigen is a viral antigen.

5. The method of claim 4, wherein said viral antigen is a hepatitis C antigen.

6. The method of claim 4, wherein said viral antigen is a hepatitis B antigen.

7. The method of claim 4, wherein said viral antigen is a human immunodeficiency virus antigen.

8. The method of claim 1, wherein said antigen is an autoantigen.

9. The method of claim 8, wherein said autoantigen is glutamic acid decarboxylase.

10. The method of claim 1, wherein said member A is a ligand and said member B is a receptor.

11. The method of claim 10, wherein said ligand is a cytokine and said receptor is a cytokine receptor.

12. The method of claim 1, wherein said member A is an enzyme and said member B is a substrate.

13. The method of claim 12, wherein said enzyme is caspase-3 and said substrate is poly(ADP-ribose) polymerase.

14. The method of claim 12, wherein said enzyme is caspase-1 and said substrate is proInterleukin-1.

15. The method of claim 1, wherein said first and second labels are fluorophores.

16. The method of claim 1, wherein said biological sample is selected from the group consisting of blood, plasma, serum, urine, cerebrospinal fluid, sputum, tears, amniotic fluid, vitreous humor, saliva, and tissue culture supernatants.

17. The method of claim 1, wherein said capture antibodies are monoclonal.

18. The method of claim 1, wherein said first antibodies are monoclonal.

19. The method of claim 1, wherein said second antibodies are monoclonal.

20. A kit for simultaneously measuring both members A and B in a binding pair complex in a biological sample, said kit comprising:
  a) a solid phase reagent, said solid phase reagent comprising a particle coated with capture antibodies having specific binding affinities for said member A of said binding pair complex, wherein substantially all said capture antibodies are oriented on said particle such that the antigen binding regions of said capture antibodies are available for binding said member A of said binding pair complex;
  b) first antibodies having specific binding affinities for said member A of said binding pair complex, wherein said first antibodies are labeled with a first label; and
  c) second antibodies having specific binding affinities for said member B of said binding pair complex, wherein said second antibodies are labeled with a second label, and wherein said first and second labels are different.

* * * * *